United States Patent [19]
Franz

[11] 3,988,142
[45] Oct. 26, 1976

[54] INCREASING CARBOHYDRATE DEPOSITION IN PLANTS WITH N-PHOSPHONO-METHYLGLYCINE AND DERIVATIVES THEREOF

[75] Inventor: John E. Franz, Crestwood, Mo.

[73] Assignee: Monsanto Company, St. Louis, Mo.

[22] Filed: Oct. 1, 1974

[21] Appl. No.: 510,923

Related U.S. Application Data

[63] Continuation-in-part of Ser. No. 223,351, Feb. 3, 1972, Pat. No. 3,853,530, which is a continuation-in-part of Ser. No. 123,057, March 10, 1971, abandoned.

[52] U.S. Cl. ............................ 71/86; 71/76
[51] Int. Cl.² ............................ A01N 9/36
[58] Field of Search ................. 71/86, 87

[56] References Cited

UNITED STATES PATENTS

| | | | |
|---|---|---|---|
| 2,959,590 | 11/1960 | Moss | 71/86 |
| 3,419,620 | 12/1968 | Becher et al. | 71/86 |
| 3,482,019 | 12/1969 | Weil et al. | 71/86 |
| 3,556,762 | 1/1971 | Hamm | 71/86 |
| 3,868,407 | 2/1975 | Franz et al. | 71/86 |

Primary Examiner—Glennon H. Hollrah
Attorney, Agent, or Firm—Arnold H. Cole; Donald W. Peterson

[57] ABSTRACT

N-phosphonomethylglycine and derivatives thereof useful to increase the carbohydrate deposition in plants.

26 Claims, No drawings

INCREASING CARBOHYDRATE DEPOSITION IN PLANTS WITH N-PHOSPHONO-METHYLGLYCINE AND DERIVATIVES THEREOF

This application is a continuation-in-part of application Ser. No. 223,351 filed Feb. 3, 1972, now U.S. Pat. No. 3,853,530, which is in turn a continuation-in-part of application Ser. No. 123,057 filed Mar. 10, 1971, now abandoned.

This invention relates to a method for regulating the natural growth or development of plants by means of chemical treatment. More particularly, this invention is concerned with a method wherein plants are treated with a chemical substance which alters their natural growth or development to enhance various agricultural or horticultural features of the plants. As employed herein, the term "natural growth or development" designates the normal life cycle of the plant in accordance with its genetics and its environment, in the absence of artificial, external influences.

It is to be understood, at the outset, that the regulation of natural growth and development hereinafter discussed does not include killing or herbicidal action. Although phytotoxic or lethal amounts of the materials disclosed herein might be employed to obtain a total inhibition of certain plants, it is contemplated here to employ only such amounts of said materials as will serve to regulate the natural growth and development. As may be expected, and as long understood by those skilled in the art, such effective plant regulating amounts will vary, not only with the particular material selected for treatment, but also with the regulatory effect to be achieved, the species of plant being treated and its stage of development, and whether a permanent or transient regulating effect is sought. Other factors which may bear upon the determination of an appropriate plant regulating amount include the plant growth medium, the manner in which the treatment is to be applied, weather conditions such as temperature or rainfall, and the like.

In accordance with the instant invention it has been found that desirable regulation of natural plant growth or development is achieved by application of a selected material to seeds, seedlings before or after emergence, roots, stems, leaves, flowers, fruit or other plant parts. Such application may be made directly to one or more of these plant parts, or application may be made indirectly as by treatment of the plant growth medium.

The chemical substances employed to increase the deposition or carbohydrates in growing plants consist of compounds illustrated by the formula

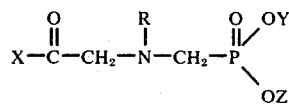

wherein:
R is selected from the group consisting of hydrogen, formyl, acetyl, benzoyl, nitrobenzoyl and chlorinated benzoyl;
Y and Z are each independently selected from the group consisting of hydrogen and lower alkyl;
X is selected from the group consisting of hydroxy, alkoxy and chloroalkoxy of up to 12 carbon atoms, alkoxy-alkoxy, alkoxyalkoxyalkoxy and chloroalkoxyalkoxy of up to 8 carbon atoms, lower alkenoxy, cyclohexyloxy, morpholino, pyrrolidinyl, piperidino; and NHR'; and
R' is selected from the group consisting of hydrogen, lower alkyl and alkenyl and cyclohexyl;
and certain salts of these compounds, which salts are selected from the group consisting of the Group I and II metals having an atomic number up to 30, hydrochloride, pyridine, ammonium, lower aliphatic hydrocarbon amine, lower alkanol amine and aniline.

As employed herein, the term "lower" designates those aliphatic radicals which have up to 4 carbon atoms in a straight or branched chain. In the case of saturated chains, the group begins with methyl, while the unsaturated chain groups begin with vinyl and ethynyl. Illustrative of the alkoxyalkoxy, alkoxyalkoxyalkoxy and chloroalkoxyalkoxy radicals representative of X are methoxymethoxy, propoxyethoxy, ethoxypropoxy, butoxybutoxy, methoxyethoxyethoxy, ethoxyethoxyethoxy, 2-chloroethoxypropoxy and the like.

The salts which are encompassed by this invention can be mono, di or tri salts of the cations recited above, and, where the cation is a divalent metal, such salts include those formed with either one or two molecules of the parent acid. As regards the amine salts, it should be understood that these include the primary, secondary and tertiary amines of the defined aliphatic hydrocarbon and alkanol groups.

Compounds of the above formula, and their salts, can be readily prepared by the procedures described in detail in applications Ser. No. 123,057, filed Mar. 10, 1971, Ser. No. 168,388, filed Aug. 2, 1971, both now abandoned, and Ser. No. 170,385, filed Aug. 9, 1971, now U.S. Pat. No. 3,799,758.

Regulation of the natural growth or development of plants by chemical treatment may result from the effect of the chemical substance on the physiological processes of the plants, or it may be due to the effect of such substance on the morphology of the plant. As should be readily apparent, said regulation may also result from a combined or sequential effect of the chemical in the areas of both physiology and morphology.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes in the physiological processes occur within the treated plant and are usually hidden from the eye of an observer. Changes of this type are most often in the production, location, storage or use of naturally occurring chemicals, including hormones, within the plant. Physiological changes in a plant may be recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

A wide variety of the regulatory responses demonstrated by the compounds of this invention are described in application Ser. No. 223,351, filed Feb. 3, 1972, now U.S. Pat. No. 3,853,530. Of particular interest here is the employment of such compounds in the treatment of carbohydrate depositing plants. Such plants include the silage crops, potatoes, sugar cane, beets, grapes, melons and fruit trees. It has been found that application of the present compounds to these plants results in an increase in the carbohydrate content of the treated plants at harvest. Although it is not absolutely certain, it is believed that the chemical treatment serves to retard the vegetative growth of the plant, at least temporarily. Such retardation permits more of the available carbohydrate in the plant to be converted to starch or sucrose, rather than being used as plant food for continued growth.

The specific examples which follow are presented as merely illustrative, non-limiting demonstrations of the useful and unexpected properties of various compounds of this invention.

EXAMPLE I

In determining the regulatory effects of compounds of this invention on sugar cane, it should be noted that the appropriate rate of application can vary from about 0.05 lb. per acre to about 5.0 lbs. per acre. Depending upon local cultural practices, sugar cane is grown for from about 9 to about 30 months before harvest, and it is thus necessary to consider both the chronological age and the maturity stage of the cane in rate determinations. Application of the treatment to the cane is generally made from about 2 to 10 weeks prior to the scheduled harvest date.

In this test individual sugar cane stalks are treated with compounds of this invention about 4–5 weeks before harvest. To avoid sampling errors, older cane, preferably 13 to 23 months old, are employed in the tests. For each compound employed, at least five stalks are used, processed and the total values obtained are averaged for each stalk. In order to improve the accuracy of the analyses, only the terminal 15 joints of each stalk are used. An identical number of untreated sugar cane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in Hawaiian Planter's Record, Volume 57, pp. 133–150. The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugar cane juice.

About 38 mg. of each compound employed (on acid equivalent basis) is dissolved in a small amount of water which contains a small amount of a surface active agent. The resultant solution is then applied to the tip of each of the stalks to be tested with the exception of the untreated controls. After harvest, the top 15 joints of each stalk of a treated group are removed, combined and analyzed as described.

The following compounds of this invention were applied to sugar cane plants in a number of tests using the procedure just described.

1. N-phosphonomethylglycine
2. mono-dimethylamine salt of N-phosphonomethylglycine
3. monosodium salt of N-phosphonomethylglycine
4. methyl N-phosphonomethylglycinate
5. ethyl N-phosphonomethylglycinate
6. 2-chloroethyl N-phosphonomethylglycinate
7. n-propyl N-phosphonomethylglycinate
8. n-butyl N-phosphonomethylglycinate
9. n-hexyl N-phosphonomethylglycinate
10. cyclohexyl N-phosphonomethylglycinate
11. n-octyl N-phosphonomethylglycinate
12. n-decyl N-phosphonomethylglycinate
13. n-dodecyl N-phosphonomethylglycinate
14. dilithium salt of N-phosphonomethylglycine
15. mono-methylamine salt of N-phosphonomethylglycine
16. mono-diisopropylamine salt of N-phosphonomethylglycine
17. mono-diethanolamine salt of N-phosphonomethylglycine
18. tetramethylene N-phosphonomethylglycinamide
19. disodium salt of N-phosphonomethylglycine
20. trisodium salt of N-phosphonomethylglycine
21. monoammonium salt of N-phosphonomethylglycine
22. calcium salt of N-phosphonomethylglycine
23. monopotassium salt of N-phosphonomethylglycine
24. hemimagnesium salt of N-phosphonomethylglycine
25. hemicopper salt of N-phosphonomethylglycine
26. N-phosphonomethylglycinamide
27. mono-diethylamine salt of N-phosphonomethylglycine
28. monopyridine salt of N-phosphonomethylglycine
29. monoaniline salt of N-phosphonomethylglycine
30. N-phosphonomethylglycine hemihydrochloride hemihydrate
31. mono-dipropargylamine salt of N-phosphonomethylglycine
32. monosodium salt of ethyl N-phosphonomethylglycinate
33. mono-ethanolamine salt of N-phosphonomethylglycine
34. mono-diallylamine salt of N-phosphonomethylglycine
35. methyl N-acetyl-N-(diethoxyphosphinylmethyl) glycinate
36. triethyl N-formyl-N-(phosphonomethyl) glycinate
37. trimethyl N-formyl-N-(phosphonomethyl) glycinate
38. ethyl N-(dimethoxyphosphinylmethyl) glycinate
39. N'-allyl-N-phosphonomethylglycinamide
40. mono-ethylamine salt of N-phosphonomethylglycine
41. mono-butylamine salt of N-phosphonomethylglycine
42. mono-isobutylamine salt of N-phosphonomethylglycine
43. monosodium salt of N-p-nitrobenzoyl-N-phosphonomethylglycine 44. N-phosphonomethylglycine morpholide
45. mono-isopropylamine salt of N-phosphonomethylglycine
46. N'-n-butyl-N-phosphonomethylglycinamide
47. N'-cyclohexyl-N-phosphonomethylglycinamide
48. N'-methyl-N-phosphonomethylglycinamide
49. triethyl N-phosphonomethylglycinate
50. monopotassium salt of ethyl N-(ethoxyphosphinylmethyl) glycinate
51. 2-(2-chloroethoxy)ethyl N-phosphonomethylglycinate In order to convert a change in Pol percent Cane into a corresponding change in the quantity of sugar obtained, it is first necessary to know the average normal yield of sugar in the area under test. Here, the tests are carried out in a region where about 100 to 110 tons of cane are harvested per acre, and about 10 tons of sugar are obtained from this quantity of cane. With this average normal yield of 10 tons per acre, an increase of just 0.1 in Pol percent Cane translates to an increase of about 200 pounds of sugar per acre.

The results obtained in tests with the listed compounds are as follows:

| Compound | HARVEST Four Weeks | | Five Weeks | |
|---|---|---|---|---|
| | Juice Purity | Pol % Cane | Juice Purity | Pol % Cane |
| 1 | 83.0 | 11.0 | 79.0 | 9.2 |
| 2 | 80.6 | 10.3 | 88.4 | 12.9 |
| Control | 77.0 | 8.0 | 80.0 | 9.3 |
| 1 | 83.3 | 13.5 | 86.0 | 13.9 |
| 2 | 79.9 | 11.1 | 82.2 | 13.6 |
| Control | 62.7 | 7.2 | 72.1 | 8.0 |
| 2 | 73.3 | 10.4 | 82.4 | 12.7 |
| Control | 66.9 | 7.2 | 71.5 | 8.0 |
| 1 | 81.7 | 11.8 | 89.3 | 15.2 |
| 3 | 82.9 | 12.6 | 86.2 | 13.9 |
| 4 | 84.7 | 12.8 | 83.5 | 13.1 |
| 5 | 82.4 | 12.7 | 80.3 | 12.1 |
| 6 | 81.9 | 12.1 | 86.6 | 13.5 |
| 7 | 81.8 | 12.1 | 85.2 | 12.9 |
| 8 | 79.9 | 11.4 | 88.3 | 15.1 |
| 9 | 83.7 | 13.0 | 85.7 | 13.3 |
| 10 | 83.5 | 12.6 | 87.4 | 13.6 |
| 11 | 80.0 | 11.5 | 82.6 | 12.0 |
| 12 | 84.2 | 13.8 | 79.9 | 11.5 |
| 13 | 76.9 | 10.3 | 82.4 | 12.2 |
| Control | 71.8 | 8.6 | 77.7 | 9.6 |
| 1 | 79.4 | 10.2 | 86.7 | 13.7 |
| Control | 74.5 | 8.9 | 77.7 | 9.7 |
| 14 | 80.9 | 11.3 | 79.3 | 11.0 |
| 15 | 76.5 | 10.2 | 68.4 | 7.9 |
| 16 | 75.3 | 9.8 | 76.1 | 9.7 |
| 17 | 82.5 | 11.8 | 79.8 | 11.2 |
| 18 | 82.1 | 12.0 | 77.8 | 10.5 |
| 19 | 77.0 | 10.4 | 78.5 | 10.8 |
| 20 | 81.1 | 11.6 | 79.8 | 11.1 |
| 21 | 75.0 | 9.8 | 77.0 | 9.9 |
| 22 | 78.9 | 10.9 | 83.5 | 12.1 |
| 23 | 80.3 | 11.0 | 84.6 | 12.4 |
| 24 | 74.2 | 9.4 | 80.0 | 10.4 |
| 25 | 77.4 | 10.4 | 81.1 | 12.0 |
| 26 | 79.5 | 11.3 | 83.1 | 12.6 |
| Control | 77.2 | 9.9 | 69.8 | 7.9 |
| 27 | 77.5 | 10.4 | 75.1 | 10.1 |
| 28 | 79.4 | 10.9 | 77.4 | 10.0 |
| 29 | 77.0 | 10.1 | 80.6 | 12.5 |
| 30 | 83.4 | 12.0 | 84.3 | 14.8 |
| 31 | 79.5 | 10.7 | 81.8 | 12.1 |
| 32 | 73.1 | 8.7 | 80.5 | 13.0 |
| 33 | 78.9 | 10.5 | 78.1 | 11.2 |
| 34 | 78.8 | 10.5 | 76.5 | 10.1 |
| 35 | 72.8 | 9.1 | 72.5 | 9.1 |
| 36 | 68.9 | 7.3 | 74.3 | 9.9 |
| 37 | 74.2 | 9.1 | 73.6 | 10.5 |
| Control | 72.9 | 8.2 | 69.7 | 7.9 |

-continued

| Compound | HARVEST Four Weeks | | Five Weeks | |
|---|---|---|---|---|
| | Juice Purity | Pol % Cane | Juice Purity | Pol % Cane |
| 3 | 78.8 | 10.7 | 85.2 | 13.5 |
| 4 | 72.2 | 8.9 | 80.6 | 10.7 |
| 6 | 72.8 | 9.2 | 80.4 | 11.4 |
| 9 | 76.2 | 9.5 | 80.9 | 12.1 |
| 10 | 82.7 | 10.6 | 87.5 | 12.2 |
| 12 | 85.2 | 11.8 | 83.1 | 12.1 |
| Control | 73.8 | 8.8 | 73.4 | 8.7 |
| 38 | 82.7 | 12.1 | 87.4 | 12.9 |
| 39 | 87.8 | 13.6 | 86.4 | 13.2 |
| 41 | 79.4 | 10.9 | 84.9 | 12.3 |
| 42 | 85.1 | 12.0 | 86.4 | 13.2 |
| 43 | 79.0 | 10.6 | 85.4 | 12.2 |
| 44 | 83.9 | 11.9 | 86.0 | 12.5 |
| 46 | 79.0 | 9.7 | 74.8 | 9.2 |
| Control | 79.9 | 10.1 | 80.7 | 10.4 |
| 33 | 81.7 | 11.0 | 76.5 | 9.2 |
| 45 | 72.7 | 8.4 | 76.4 | 9.2 |
| Control | 77.9 | 9.8 | 77.8 | 9.3 |
| 40 | 77.8 | 9.5 | 70.0 | 9.3 |
| 47 | 82.8 | 11.0 | 75.3 | 9.6 |
| 48 | 89.3 | 13.6 | 83.3 | 12.6 |
| 49 | 85.9 | 11.7 | 83.0 | 12.2 |
| Control | 76.0 | 8.7 | 74.8 | 8.7 |
| 2 | 82.0 | 14.1 | 76.6 | 9.9 |
| 8 | 85.9 | 13.1 | 89.7 | 15.0 |
| Control | 83.3 | 11.7 | 78.5 | 9.6 |
| 3 | 77.1 | 9.9 | 79.4 | 10.9 |
| 23 | 83.3 | 11.3 | 88.6 | 14.1 |
| 29 | 82.4 | 11.0 | 85.6 | 13.1 |
| 31 | 83.0 | 11.9 | 84.0 | 13.2 |
| 32 | 83.2 | 10.9 | 81.0 | 11.5 |
| Control | 77.2 | 8.9 | 80.0 | 10.4 |
| 33 | 78.8 | 11.2 | — | — |
| 43* | 82.6 | 11.7 | — | — |
| 49 | 80.2 | 10.4 | — | — |
| Control | 76.9 | 9.8 | — | — |
| 5 | 82.3 | 11.1 | 77.8 | 11.1 |
| 7 | 77.9 | 9.4 | 83.6 | 12.2 |
| 11 | 81.4 | 11.2 | 84.0 | 13.1 |
| 14 | 74.4 | 9.2 | 82.9 | 12.3 |
| 20 | 84.5 | 11.2 | 85.1 | 16.2 |
| 22 | 78.7 | 9.7 | 84.0 | 12.9 |
| Control** | 75.9 | 9.1 | 65.7 | 7.24 |
| 38 | 78.5 | 10.2 | 84.1 | 12.0 |
| Control | 78.4 | 10.9 | 73.5 | 8.9 |
| 22 | 77.2 | 9.2 | 71.7 | 8.0 |
| 24 | 88.2 | 14.4 | 82.1 | 11.6 |
| 25 | 76.5 | 11.1 | 74.5 | 9.5 |
| 26 | 73.8 | 8.2 | 83.6 | 11.9 |
| 28 | 71.5 | 9.0 | 84.3 | 12.1 |
| 39 | 82.8 | 10.9 | 75.0 | 9.5 |
| 42 | 82.7 | 12.1 | 76.0 | 9.9 |
| 44 | 79.4 | 10.4 | 88.0 | 13.7 |
| Control | 78.4 | 9.1 | 66.2 | 7.8 |
| 3 | 88.0 | 13.9 | 82.9 | 12.0 |
| Control | 79.7 | 9.8 | 80.1 | 10.1 |
| 3 | 78.5 | 10.3 | 82.9 | 11.4 |
| Control | 76.9 | 8.8 | 77.6 | 9.6 |
| 38 | 78.9 | 11.6 | 83.8 | 12.7 |
| 41 | 77.7 | 10.4 | 81.4 | 11.7 |
| 46 | 76.1 | 9.7 | 74.9 | 9.7 |
| Control | 75.5 | 9.0 | 77.6 | 9.4 |
| 3 | 80.4 | 11.7 | 80.5 | 12.0 |
| Control | 76.2 | 8.5 | 78.4 | 9.5 |
| 15 | 84.4 | 11.6 | 75.9 | 9.0 |
| 16 | 78.5 | 10.8 | 81.5 | 11.4 |
| 21 | 80.2 | 10.8 | 78.8 | 11.4 |
| 27 | 74.1 | 10.3 | 85.0 | 13.4 |
| 34 | 74.5 | 10.6 | 82.4 | 13.3 |
| Control | 78.3 | 9.7 | 77.9 | 9.8 |
| 1 | 84.3 | 14.1 | 86.1 | 14.7 |
| 8 | 87.2 | 13.9 | 87.3 | 14.3 |
| 23 | 84.3 | 12.8 | 84.1 | 13.7 |

-continued

| Compound | HARVEST Four Weeks | | Five Weeks | |
|---|---|---|---|---|
| | Juice Purity | Pol % Cane | Juice Purity | Pol % Cane |
| 29 | 79.9 | 12.2 | 82.9 | 12.0 |
| 45 | 78.7 | 11.5 | 81.9 | 12.1 |
| 48 | 85.5 | 13.2 | 85.8 | 13.9 |
| Control | 72.0 | 8.7 | 80.8 | 10.5 |
| 50 | 78.2 | 10.1 | 80.6 | 10.5 |
| Control | 72.3 | 7.5 | 70.8 | 7.5 |
| 15 | 77.7 | 10.1 | 84.3 | 13.4 |
| 27 | 63.6 | 5.5 | 78.5 | 11.3 |
| Control | 71.2 | 7.3 | 70.9 | 8.0 |
| 50 | 73.2 | 9.5 | 84.1 | 12.6 |
| 51 | 82.0 | 12.3 | 86.7 | 14.0 |
| Control | 70.3 | 7.4 | 75.1 | 9.2 |
| 50 | 77.5 | 9.9 | 76.7 | 9.6 |
| Control | 76.5 | 9.7 | 67.3 | 7.2 |
| 51 | 75.5 | 9.3 | 81.3 | 11.6 |
| Control | 71.4 | 7.7 | 76.0 | 9.0 |
| 51 | 83.4 | 12.3 | 84.3 | 13.6 |
| Control | 66.4 | 7.3 | 68.2 | 7.0 |

*In this particular test group, all of the samples taken five weeks after treatment spoiled before the analytical work could be done.
**In this particular test, the untreated control samples had to be discarded without analytical work. The control data is obtained from sugar cane plants treated with a standard chemical, Trysben.

EXAMPLE II

The regulatory effect of compounds of this invention on table beets was demonstrated in the following test. Compound 1, identified above, was the particular chemical employed, and treatment was made to beets of the Early Wonder variety which had been grown for 50 days. The chemical was formulated in acetone and water, and about 0.05% of a surface active agent was used.

Applications were made at rates of 1.0, 0.5 and 0.25 mg. per plant using a hand sprayer, and roots were harvested at 2 and 4 weeks after the treatment. Sucrose and total carbohydrate content were determined using the anthrone method with juice expressed from borings taken from the roots. Data was also obtained on untreated plants and on plants treated with only the solvent and surfactant. The observed results combine several replications of each test.

Data obtained 2 weeks after treatment show that the beets treated with only solvent and surfactant contained 11% more sucrose than the untreated beets, while beets treated at the various rates of Compound 1 incidated show sucrose increases of from about 15% to 32% over said untreated beets. Further, the treated beets at 2 weeks showed from about 4% to about 18% more sucrose than those treated without Compound 1.

Determinations of total carbohydrate content 2 weeks after treatment again showed that all of the treated plants displayed at least a 10% increase over the untreated beets. It is to be noted, however, that beets treated with Compound 1 at the lowest rate, 0.25 mg. per plant, were found to contain less total carbohydrates than those treated only with solvent and surfactant.

When data was obtained 4 weeks after application, it was found that the highest content of both sucrose and total carbohydrates was in the untreated table beets. These latter results serve to illustrate that certain regulatory effects of compounds of this invention may be temporary or transient.

EXAMPLE III

The testing procedures described in Example I are repeated with six of the compounds of this invention, and each compound is applied at several different rates. In the case of Compound 1, the free acid, the basic rate of 38 mg. per plant is employed, along with rates which are double, one half and one fourth of said basic rate. The other compounds in this test are an ester, an amide, and three different salts. For each of these, the basic rate is calculated on an acid equivalent basis, and the same multiples of such basic rate are also applied. The results obtained are as follows:

| Compound | Rate mg./plant | HARVEST Four Weeks | | Five Weeks | |
|---|---|---|---|---|---|
| | | Juice Purity | Pol % Cane | Juice Purity | Pol % Cane |
| 1 | 76 | 75.7 | 9.9 | 78.7 | 10.9 |
| | 38 | 85.8 | 13.0 | 81.2 | 12.0 |
| | 19 | 88.5 | 14.5 | 85.7 | 12.6 |
| | 9.5 | 85.5 | 14.3 | 84.2 | 14.2 |
| 23 | 182 | 82.1 | 11.7 | 81.6 | 12.1 |
| | 91 | 80.3 | 11.1 | 83.5 | 13.3 |
| | 46 | 86.5 | 13.3 | 80.9 | 12.0 |
| | 23 | 84.5 | 12.0 | 81.5 | 12.0 |
| 45 | 190 | 73.9 | 9.5 | 79.9 | 11.3 |
| | 95 | 76.5 | 10.2 | 80.8 | 11.2 |
| | 48 | 76.3 | 9.6 | 77.1 | 10.4 |
| | 24 | 75.4 | 9.1 | 84.2 | 13.1 |
| Control | — | 78.2 | 9.4 | 76.7 | 9.0 |
| 8 | 102 | 86.0 | 13.4 | 82.7 | 12.4 |
| | 51 | 85.6 | 13.4 | 81.5 | 12.5 |
| | 26 | 86.5 | 13.8 | 80.6 | 12.4 |
| | 13 | 88.2 | 15.0 | 81.1 | 13.3 |
| 29 | 118 | 83.9 | 11.4 | 84.0 | 13.7 |
| | 59 | 83.6 | 12.2 | 80.7 | 11.5 |
| | 30 | 83.9 | 11.4 | 85.0 | 14.0 |
| | 15 | 78.7 | 10.6 | 82.6 | 12.2 |
| 48 | 82 | 83.3 | 12.5 | 81.4 | 12.0 |
| | 41 | 81.2 | 11.3 | 76.9 | 9.9 |
| | 21 | 83.2 | 12.5 | 80.3 | 11.5 |
| | 11 | 82.4 | 12.8 | 76.3 | 9.5 |
| Control | — | 78.1 | 9.9 | 76.3 | 9.0 |

EXAMPLE IV

The test methods described in Example I are again followed on field plots of sugar cane about 100 ft$^2$. In these tests, the compounds of this invention are applied with a manual sprayer, and the formulations are used at approximately 8.0 gallons per acre. The plants are harvested at different times after treatment, and the results obtained are as follows:

| Harvest (Weeks after application) | Control | JUICE PURITY | | | | | |
|---|---|---|---|---|---|---|---|
| | | Compound 1 | | Compound 45 | | Compound 8 | |
| | | 0.5 lb/acre | 1.0 lb/acre | 1.0 lb/acre | 2.0 lb/acre | 1.0 lb/acre | 2.0 lb/acre |
| 0 | 76.3 | 76.3 | 76.3 | 76.3 | 76.3 | 76.3 | 76.3 |
| 3 | 77.5 | 79.9 | 85.3 | 81.7 | 78.5 | 81.1 | 76.3 |
| 4 | 71.6 | 79.3 | 80.7 | 79.4 | 82.8 | 73.2 | 85.1 |
| 5 | 70.6 | 86.8 | 84.7 | 86.1 | 87.2 | 83.4 | 86.7 |

| | -continued | | | | | | |
|---|---|---|---|---|---|---|---|
| 6 | 70.6 | 85.2 | 86.4 | 85.2 | 85.9 | 82.2 | 88.8 |
| 7 | 68.1 | 84.8 | 85.7 | 89.6 | 85.3 | 86.1 | 88.4 |
| 8 | 75.7 | 86.9 | 86.8 | 87.4 | 88.0 | 82.3 | 86.8 |

| Harvest (Weeks after application) | Control | POL % CANE | | | | | |
|---|---|---|---|---|---|---|---|
| | | Compound 1 | | Compound 45 | | Compound 8 | |
| | | 0.5 lb/acre | 1.0 lb/acre | 1.0 lb/acre | 2.0 lb/acre | 1.0 lb/acre | 2.0 lb/acre |
| 0 | 9.1 | 9.1 | 9.1 | 9.1 | 9.1 | 9.1 | 9.1 |
| 3 | 9.2 | 11.2 | 12.4 | 11.4 | 10.3 | 11.1 | 9.4 |
| 4 | 8.3 | 11.6 | 11.7 | 11.6 | 13.1 | 8.8 | 13.3 |
| 5 | 7.9 | 14.1 | 13.6 | 14.0 | 15.0 | 13.1 | 14.2 |
| 6 | 7.7 | 14.0 | 13.1 | 14.5 | 14.4 | 11.9 | 15.5 |
| 7 | 6.9 | 13.1 | 13.7 | 16.5 | 13.4 | 15.2 | 15.4 |
| 8 | 9.0 | 14.8 | 14.7 | 15.1 | 15.2 | 12.1 | 14.1 |

EXAMPLE V

In this test, sugarbeet plants of the Great Western Monohy $D_2$ variety are grown hydroponically from seeds in a greenhouse. A spray solution of the chemical to be tested is prepared by first dissolving 100 mg. of said chemical in 1 ml. of acetone. From this stock solution, a 0.9 ml. portion is taken and diluted to 10 ml. with acetone. Then, 15 ml. of a 0.4% aqueous solution of Ethomeen T/12 is added to 5 ml. of the dilute solution. This 20 ml. formulation is sprayed onto three sugarbeet plants which are 8 weeks old, the application rate of the test chemical being approximately 1.0 pound per acre. Lower rates are obtained in the same manner by further dilution of the stock solution.

The treated plants, along with untreated control plants are returned to the greenhouse, where they are grown for three weeks. The plants are then uprooted and washed. Tops are cut away, and the crown and hair roots are trimmed from the root portion. The latter portion is chopped in a food cutter for two minutes, and a portion of the macerate is placed in a basic lead acetate solution. This solution is shaken vigorously, placed in a warm water bath, cooled and filtered. Then, the resulting clear sugar solution is poured into a saccharimeter, and a direct reading of percent sucrose is obtained.

Using Compound 1 in this test at a rate of 0.1 pounds per acre, a 9% increase in sucrose is noted by comparison with the control plants. With the same compound at 1.0 pound per acre, the sugarbeet tops were dead, the roots had begun to rot, and sucrose content was far lower than the control plants. With Compound 8, an increase of 12% is observed at a rate of 0.1 pounds per acre, and an increase of 17% is found at an application rate of 1.0 pound per acre.

The same test procedures are carried out with 2-ethoxyethyl N-phosphonomethylglycinate at rates of 0.3 and 0.06 pounds per acre. The higher rate causes a 21% decrease in sucrose content, but a 31% increase in sucrose content is noted at the lower rate. This test is repeated with said compound at rates of 0.12, 0.06 and 0.03 pounds per acre, and increases in sucrose content of 39%, 24% and 13% respectively are observed.

From the illustrative data presented in the foregoing examples of individual compounds of this invention on representative plants, it should be clear that regulatory response will be dependent upon the compound employed, the rate of application, the plant species and its stage of development, and other factors well understood by those skilled in the art.

The plant regulating compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid or organic origin, water, a wetting agent, a dispersing agent, an emulsifying agent or any suitable combination of these. From the viewpoint of economy and convenience, water is the preferred diluent, particularly with the highly water-soluble glycine salts such as the alkali metal salts and amine and ammonium salts. With these derivatives, solutions containing as high as five pounds or more of active materials per gallon can be readily prepared.

The plant regulating compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contains from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

When operating in accordance with the present invention, effective carbohydrate increasing amounts of the glycines are applied directly or indirectly to the plants. The application of liquid and particulate solid plant regulating compositions can be carried out by conventional methods, e.g. power dusters, boom and hand sprayers and spray dusters. The compositions can also be applied from airplanes as a dust or a spray because of their effectiveness at low dosages.

The application of an effective carbohydrate increasing amount of the compounds of this invention to the plant is essential and critical for the practice of the present invention. The exact amount of active ingredient to be employed is dependent upon such factors as the plant species and stage of development thereof, and the environmental conditions, as well as the specific glycine employed. In general, the active ingredients are employed in effective carbohydrate increasing amounts equivalent to from about 0.01 to about 5.0 lbs./acre. It should be understood that the amount of active ingredient employed must be sufficient to increase the carbohydrate deposition of the treated plants without producing a herbicidal or killing effect on such plants. It is believed that those skilled in the art can readily determine from the teachings of this specification, including examples, the appropriate application rates.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. A method of increasing carbohydrate deposition in plants which comprises applying to said plants an effective, carbohydrate increasing, non-lethal amount of a compound selected from those having the formula

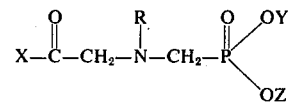

wherein:
R is selected from the group consisting of hydrogen, formyl, acetyl, benzoyl, nitrobenzoyl and chlorinated benzoyl;
Y and Z are each independently selected from the group consisting of hydrogen and lower alkyl;
X is selected from the group consisting of hydroxy, alkoxy and chloroalkoxy of up to 12 carbon atoms, alkoxyalkoxy, alkoxyalkoxyalkoxy and chloroalkoxyalkoxy of up to 8 carbon atoms, lower alkenoxy and cyclohexyloxy;

and certain salts thereof, which salts are selected from the group consisting of the Group I and II metals having an atomic number up to 30, hydrochloride, pyridine, ammonium, lower aliphatic hydrocarbon amine, lower alkanol amine and aniline.

2. A method as defined in claim 1 wherein said compound is a salt.

3. A method as defined in claim 2 wherein said salt is selected from Group I and Group II metals having an atomic number up to 30.

4. A method as defined in claim 2 wherein said salt is a lower aliphatic hydrocarbon amine salt.

5. A method as defined in claim 2 wherein R is hydrogen.

6. A method as defined in claim 5 wherein the plants are sugar cane plants.

7. A method as defined in claim 5 wherein the plants are beet plants.

8. A method as defined in claim 5 wherein said compound is mono-isopropylamine salt of N-phosphonomethylglycine.

9. A method as defined in claim 5 wherein said compound is monopotassium salt of N-phosphonomethylglycine.

10. A method as defined in claim 5 wherein said compound is monoaniline salt of N-phosphonomethylglycine.

11. A method of increasing carbohydrate deposition in plants which comprises applying to said plants an effective, carbohydrate increasing, non-lethal amount of a compound of the formula

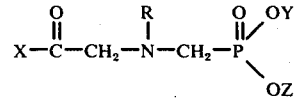

wherein:
R is selected from the group consisting of hydrogen, formyl, acetyl, benzoyl, nitrobenzoyl and chlorinated benzoyl;
Y and Z are each independently selected from the group consisting of hydrogen and lower alkyl;
X is selected from the group consisting of hydroxy, alkoxy and chloroalkoxy of up to 12 carbon atoms, alkoxyalkoxy, alkoxyalkoxyalkoxy and chloroalkoxyalkoxy of up to 8 carbon atoms, lower alkenoxy and cyclohexyloxy.

12. A method as defined in claim 11 wherein R is hydrogen.

13. A method as defined in claim 12 wherein Y and Z are hydrogen.

14. A method as defined in claim 13 wherein X is alkoxy of up to 12 carbon atoms.

15. A method as defined in claim 12 wherein the plants are sugar cane plants.

16. A method as defined in claim 12 wherein the plants are beet plants.

17. A method as defined in claim 11 wherein said compound is N-phosphonomethylglycine.

18. A method as defined in claim 11 wherein said compound is n-butyl N-phosphonomethylglycinate.

19. A method as defined in claim 11 wherein said compound is 2-ethoxyethyl N-phosphonomethylglycinate.

20. A method as defined in claim 1 wherein said plants are sugar cane plants.

21. A method as defined in claim 1 wherein said plants are beet plants.

22. A method as defined in claim 1 wherein said compound is applied to said plants from about 2 to 10 weeks prior to harvest.

23. A method as defined in claim 1 wherein said compound is applied to said plants at a rate of from about 0.01 to 5.0 pounds per acre.

24. A method as defined in claim 11 wherein said compound is applied to said plants from about 2 to 10 weeks prior to harvest.

25. A method of increasing carbohydrate deposition in carbohydrate depositing crop plants which comprises applying to said plants, from about 2 to 10 weeks prior to harvest, an effective, carbohydrate increasing, non-lethal amount of a compound selected from those having the formula $$X-\overset{O}{\overset{\|}{C}}-CH_2-\overset{R}{\overset{|}{N}}-CH_2-\overset{O}{\overset{\|}{P}}\diagdown\overset{OY}{\underset{OZ}{}}$$

wherein:
R is selected from the group consisting of hydrogen, formyl, acetyl, benzoyl, nitrobenzoyl and chlorinated benzoyl;
Y and Z are each independently selected from the group consisting of hydrogen and lower alkyl;
X is selected from the group consisting of hydroxy, alkoxy and chloroalkoxy of up to 12 carbon atoms, alkoxyalkoxy, alkoxyalkoxyalkoxy and chloroalkoxyalkoxy of up to 8 carbon atoms, lower alkenoxy and cyclohexyloxy; and certain salts thereof, which salts are selected from the group consisting of the Group I and II metals having an atomic number up to 30, hydrochloride, pyridine, ammonium, lower aliphatic hydrocarbon amine, lower alkanol amine and aniline.

26. A method as defined in claim 5 wherein said compound is disodium salt of N-phosphonomethylglycine.

* * * * *